(12) United States Patent
Huff

(10) Patent No.: US 8,911,413 B2
(45) Date of Patent: Dec. 16, 2014

(54) HEMOSTATIC VALVE WITH MULTI-LAYER VALVE STRUCTURE

(75) Inventor: Sharon M. Huff, Jeffersonville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 271 days.

(21) Appl. No.: 13/486,621

(22) Filed: Jun. 1, 2012

(65) Prior Publication Data

US 2012/0310166 A1 Dec. 6, 2012

Related U.S. Application Data

(60) Provisional application No. 61/493,085, filed on Jun. 3, 2011.

(51) Int. Cl.
| | | |
|---|---|---|
| *A61M 5/315* | (2006.01) | |
| *A61M 5/178* | (2006.01) | |
| *A61M 1/00* | (2006.01) | |
| *A61M 5/00* | (2006.01) | |
| *A61M 39/06* | (2006.01) | |

(52) U.S. Cl.
CPC ............ *A61M 39/06* (2013.01); *A61M 39/0613* (2013.01); *A61M 2039/0673* (2013.01)
USPC .......... 604/236; 604/167.03; 604/34; 604/249

(58) Field of Classification Search
CPC .................. A61B 17/3462; A61B 2017/3464; A61B 17/3439; A61B 17/3498; A61B 2017/00845; A61M 39/0613; A61M 2039/0673; A61M 2039/0626
USPC .......... 604/33, 34, 36, 167.03, 236–237, 249
See application file for complete search history.

(56) References Cited

U.S. PATENT DOCUMENTS

| | | |
|---|---|---|
| 5,006,113 A | 4/1991 | Fischer |
| 5,158,553 A | 10/1992 | Berry et al. |
| 5,556,387 A * | 9/1996 | Mollenauer et al. .......... 604/249 |

(Continued)

FOREIGN PATENT DOCUMENTS

| | | |
|---|---|---|
| WO | WO 03/048616 A1 | 6/2003 |
| WO | WO 2010/028021 A1 | 3/2010 |

OTHER PUBLICATIONS

European Appln. No. 12170554.5 Partial Search Report dated Nov. 30, 2012 (7 pages).

(Continued)

*Primary Examiner* — Rebecca E Eisenberg
(74) *Attorney, Agent, or Firm* — Brinks Gilson & Lione

(57) ABSTRACT

A hemostatic valve device for use in inserting an interventional device into a body lumen of patient is provided. The valve device includes a housing that defines a cavity between first and second end openings. A valve structure is disposed within the cavity, and defines a variable diameter channel for receiving the interventional device. The valve structure can include discrete layers of material, such as a sealing layer and a contractible layer such as a biaxial braided layer. The end of the valve structure is movable relative to the fixed end so that the longitudinal passageway of the valve structure varies in diameter and axial length to form a seal against an interventional device inserted within the passageway. An operable element is coupled to the movable end and is actuated by the end user to open and close the valve structure.

20 Claims, 4 Drawing Sheets

(56) References Cited

U.S. PATENT DOCUMENTS

| | | |
|---|---|---|
| 6,416,499 B2 | 7/2002 | Paul, Jr. |
| 7,172,580 B2 | 2/2007 | Hruska et al. |
| 7,435,253 B1 | 10/2008 | Hartley et al. |
| 2005/0020981 A1 | 1/2005 | Kurth |
| 2007/0078395 A1 | 4/2007 | Valaie |
| 2007/0276461 A1 | 11/2007 | Andreas et al. |
| 2008/0009834 A1* | 1/2008 | Mialhe .......... 604/533 |
| 2009/0118681 A1 | 5/2009 | Molgaard-Nielsen ....... 604/246 |
| 2012/0238958 A1* | 9/2012 | Moore .......... 604/167.03 |

OTHER PUBLICATIONS

"The Open Prosthetics Project", printed Jun. 1, 2012, 5 pgs., http://www.openprosthetics.org/suspension.

* cited by examiner

HEMOSTATIC VALVE WITH MULTI-LAYER VALVE STRUCTURE

PRIORITY CLAIM

This invention claims the benefit of priority of U.S. Provisional Application Ser. No. 61/493,085, entitled "Hemostatic Valve With Multi-Layer Valve Structure," filed Jun. 3, 2011, the disclosure of which is hereby incorporated by reference in its entirety.

BACKGROUND

The present disclosure relates to medical devices and procedures. In particular, it relates to hemostatic valves and systems, and methods of using the same.

Numerous procedures have been developed that involve the percutaneous insertion of a medical device into a body vessel of a patient's body. Such a device may be introduced into the vessel by a variety of known techniques. For example, a wire guide may be introduced into a vessel using the Seldinger technique. This technique involves creating a surgical opening in a vessel with a needle and inserting a wire guide into the vessel through a bore of the needle. The needle can be withdrawn, leaving the wire guide in place. An introducer device is then inserted over the wire guide and into the vessel. The introducer device may be used in conventional fashion to insert into the body vessel a variety of medical devices, such as catheters, cardiac leads, balloons, stents, stent grafts, and the like.

For example, an introducer device may be used to deliver and deploy an endoluminal prosthesis, such as a stent or stent graft, to treat a damaged or diseased body lumen such as a bile duct or a blood vessel. The deployment of the endoluminal prosthesis into the lumen of a patient from a remote location by the use of an introducer delivery and deployment device is well known in the art. For example, U.S. Pat. No. 7,435,253 to Hartley entitled "A Prosthesis and a Method and Means of Deploying a Prosthesis," which is incorporated herein by reference in its entirety, proposes a delivery and deployment system for an endoluminal prosthesis. The prosthesis is radially compressed onto a delivery catheter and is covered by an outer sheath. To deploy the system, the operator slides the outer sheath over the delivery catheter, thereby exposing the prosthesis for outward expansion thereof.

One of the challenges associated with endoluminal procedures is controlling the flow of bodily fluids within the introducer device during the procedure. Valve devices may be provided when it is necessary or desired to control fluid flow. For example, the introducer device may include a hemostatic valve to limit or prevent blood loss through the introducer device during a procedure. Various hemostatic valve devices have been described in the patent literature. U.S. Pat. App. Publ. No. 2007/0078395 A1, which is incorporated herein by reference in its entirety, for example, discloses numerous examples of hemostatic valve devices and systems that use disk valves to control fluid flow. However, disk valves can deform over time because of compression set and sterilization. Disk valves can tear or become dislodged during insertion and/or withdrawal of an interventional device. Furthermore, it is difficult for disk valves to accommodate a wide range of diameters, while providing an effective seal. Although the disk valve can be modified with increased tensile and/or elongation properties, this can increase the resistance and thus increase the forces for insertion and/or withdrawal of the interventional device through the disk valves.

Another type of hemostatic valve device that is presently in use for sealing elongated passages in a medical device to prevent loss of blood is known as an iris valve. An iris valve is described in U.S. Pat. No. 5,158,553, which is incorporated herein by reference in its entirety. The valve described in the '553 patent comprises a valve hub that is joined to a catheter-type device, and a rotatable cap that is joined to the hub. An elastomeric sleeve is positioned in an opening through the interior of the valve body. Each end of the elastomeric sleeve is joined to the rotatable cap by wrapping and clamping the respective end around a clamping mechanism. When the cap is rotated in a first direction, the circular opening of the elastomeric sleeve is fully opened. When the cap is rotated in a second direction opposite the first direction, the elastomeric sleeve is twisted intermediate the two ends to effect closure of the circular opening. Due to the elastomeric properties of the sleeve, the circular opening of the elastomeric sleeve constricts as the cap is rotated to effect closure.

Although the valve of the '553 patent is generally effective for sealing sheaths of certain sizes and compositions, the general design of the valve assembly of the '553 patent has certain shortcomings. For example, the manner of engaging the ends of the seal to the respective hub and cap is less than optimal. Such ends are capable of disengagement, which destroys the ability of the valve to form a seal. In addition, the seal does not include provisions to prevent recoil of the seal after rotation of the rotatable cap to position the seal in a desired position. As a result, if the operator relaxes the rotational pressure on the valve, the seal can revert, or recoil, to its original (unsealed) position. Yet another problem with the iris valve assembly as described in the '553 patent is that longitudinally extended gaps or channels are capable of being formed by infolding along the seal, which gaps or channels can extend through the valve after rotation of the valve to the closed position. When such gaps or channels are present, fluid can leak through them in the valve seal. Furthermore, the configuration of such valves renders them subject to tearing.

Often, a single introducer device may be used to insert multiple medical devices during a single procedure. For example, a single introducer sheath with a hemostatic valve device may be used first for introducing a delivery catheter for deployment of an endoluminal prosthesis within a vessel. Once the prosthesis is placed within the vessel, the single introducer sheath with the hemostatic valve device is also used to deliver an interventional catheter, such as a balloon catheter, to the vessel to cause expansion of the deployed prosthesis. In this example, the hemostatic valve device must be able to provide a hemostatic seal under at least three distinct conditions: 1) to seal against the delivery catheter carrying the endoluminal prosthesis when inserted in the introducer sheath and valve device; 2) to seal when the delivery catheter is removed from the introducer sheath and valve device; and 3) to seal against the interventional catheter when inserted in the introducer sheath and valve device.

One problem with using a single introducer device for multiple medical devices is that each medical device can have a different diameter. Thus, the ideal hemostatic valve device will be able to accommodate and seal over a wide range of diameters of the medical devices. For example, it may be advantageous for a hemostatic valve device to seal well around the surface of a delivery catheter, as well as a wire guide that is 50%, 25%, 10%, or smaller in diameter relative to the diameter of the delivery catheter, or to seal even when there is no device present. Moreover, such a hemostatic valve device should be able to adjust quickly to large variations in diameter, and preferably avoid some of the challenges of twisting or rotating the valve member.

SUMMARY

In one embodiment, an introducer for use in inserting an interventional device into a body vessel of a patient is provided. The introducer can include a housing and a valve structure. The housing can have a first end opening, a second end opening, and an interior surface defining a housing cavity between the first and second end openings. The valve structure is coupled within the housing cavity. The valve structure can have an inner radial surface defining a tubular channel along a longitudinal axis. A sealing region may be located at least partially between the first and second end openings. The valve structure is movable between a first configuration and a second configuration. In the first configuration, the sealing region can have a first diameter and the valve structure can have a first axial length. In the second configuration, the sealing region can have a second diameter less than the first diameter and the valve structure can have a second axial length greater than the first axial length. A contractible structure, such as, e.g., a biaxial braided structure, and a sealing structure, such as, e.g., a silicone tube, may form the valve structure. The sealing structure can be disposed inside of the contractible structure. The sealing structure can remain unattached to the contractible structure at least along the sealing region of the valve structure to permit independent expansion and contraction therebetween in response to movement of the valve structure between the first and second configurations.

In another embodiment, a hemostatic valve device is provided. The valve device includes a housing, a valve structure, and an operable element. The housing can have a first end opening, a second end opening, and an interior surface defining a housing cavity between the first and second end openings. The valve structure has a first end and a second end, and an inner radial surface defining a longitudinal passageway for an interventional device. The first end of the valve structure can be securely fixed to the housing. A sealing region may be located on the valve structure at least partially between the first and second ends to provide sealable contact with the interventional device. The operable element can be coupled to the second end of the valve structure. The operable element is movable between a first position and a second position. In the first position, the valve structure can have a first configuration in which the sealing region has a first diameter and the valve structure has a first axial length. In the second position, the valve structure can move to a second configuration in which the sealing region has a second diameter less than the first diameter and the valve structure has a second axial length greater than the first axial length.

In another embodiment, a method of introducing an interventional device to a target site in a body vessel of a patient is provided. The method can include one or more of the following steps, including inserting an interventional device through a longitudinal passageway of a hemostatic valve device in a first configuration. The valve device can include a housing having a first end opening, a second end opening, and an interior surface defining a housing cavity between the first and second end openings. A valve structure is coupled within the housing cavity. The valve structure can have an inner radial surface defining the longitudinal passageway of the valve device. A contractible structure and a sealing structure can form the valve structure. The sealing structure can be disposed inside of the contractible structure and remain unattached to the contractible structure to allow for independent movement therebetween. The valve structure in the first configuration forms a first diameter sized to receive the interventional device and a first axial length. One of the ends of the valve structure is moved relative to the other end of the valve structure so that the valve structure is moved to a second configuration. In the second configuration, the valve structure forms a second diameter smaller than the first diameter and sized to seal along the interventional device and a second axial length longer than the first axial length.

BRIEF DESCRIPTION OF THE DRAWINGS

FIG. 9 illustrates a ratcheting mechanism provided with a hemostatic valve device.

DETAILED DESCRIPTION OF PREFERRED EMBODIMENTS

Throughout the specification, when referring to a medical device, or a portion of a medical device, the terms "distal" and "distally" shall denote a position, direction, or orientation that is generally towards, or in the direction of, the patient when the device is in use. The terms "proximal" and "proximally" shall denote a position, direction, or orientation that is generally away from the patient, or closer to the operator, during use of the device. It should also be noted that in the figures like-referenced numerals designate corresponding components throughout the different views.

Figure 1:
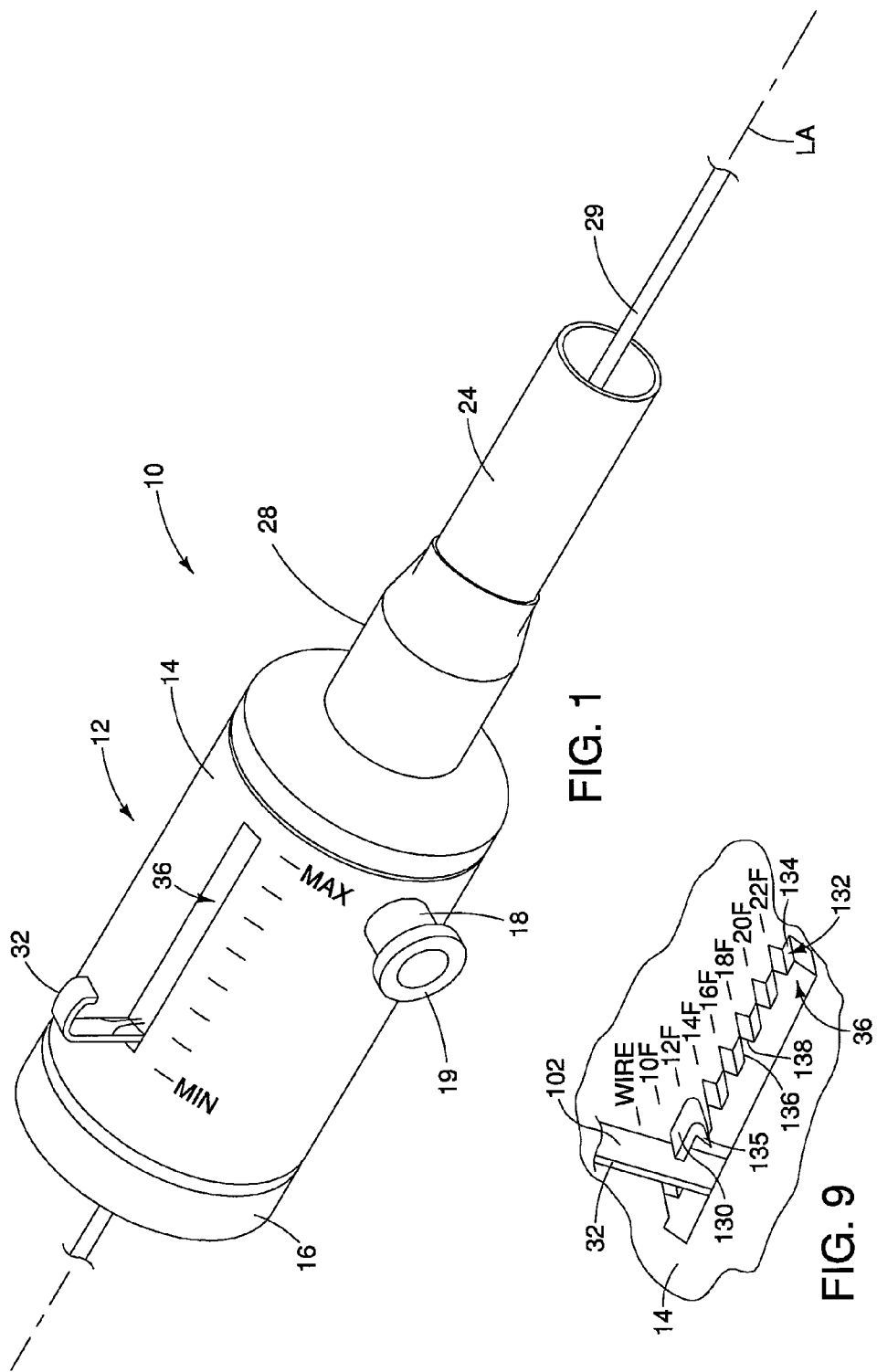
FIG. 1 is a perspective view of an introducer having a hemostatic valve device.
Figure 2:
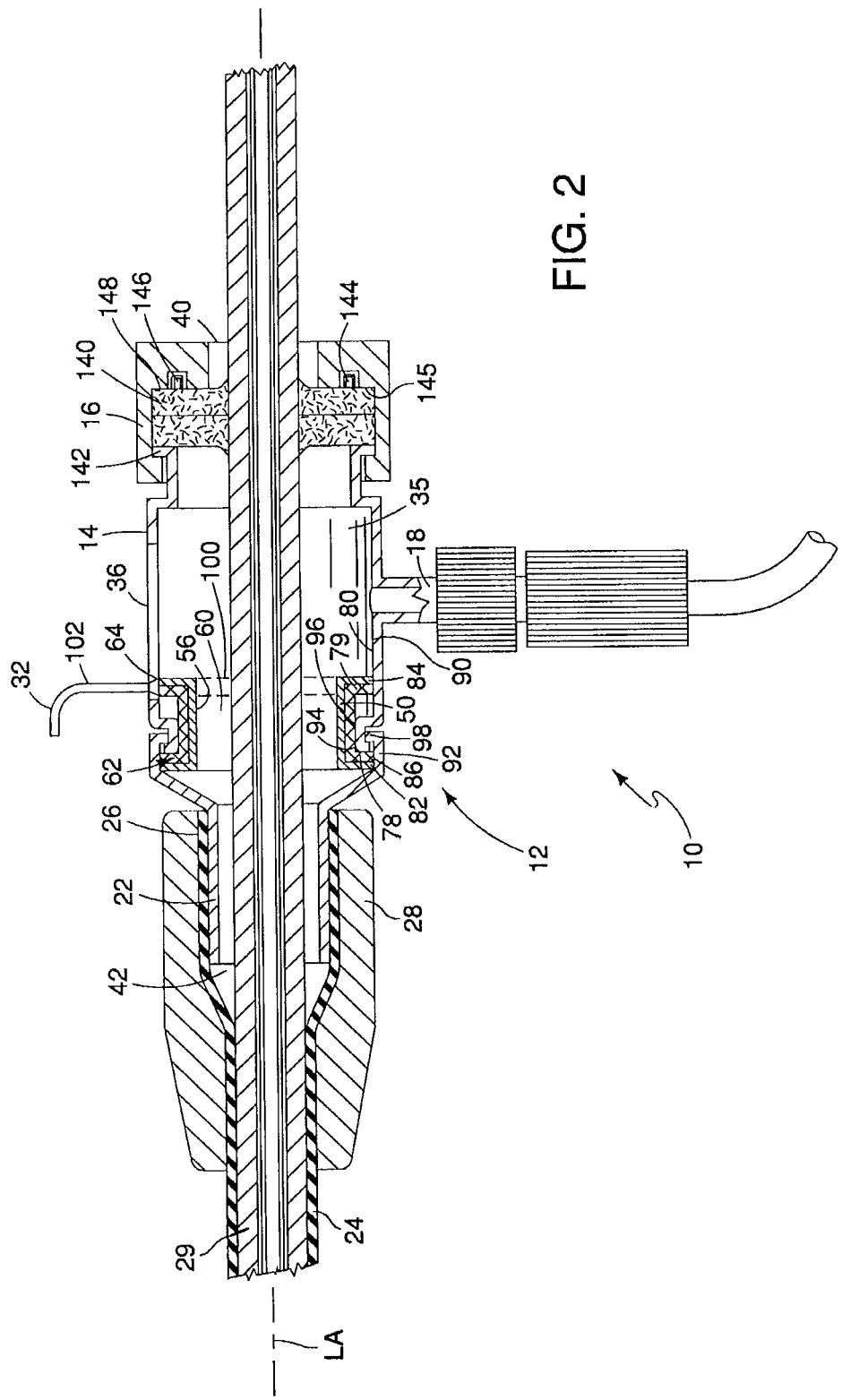
FIG. 2 is a longitudinal cross-sectional view of an introducer having a hemostatic valve device, with a valve structure in an open position and an interventional device extending therethrough.

FIG. 1 illustrates a perspective view of a hemostatic valve assembly 10. The valve assembly 10 includes a valve housing 12 having a cannula body 14 and an end cap 16. The cannula body 14 and the end cap 16 may be sealably coupled to one another. The valve housing 12 may also include a side-arm spout 18 extending in a generally transverse direction from the cannula body 14. The spout 18 may be used for supplying or removing a fluid in a conventional fashion, and preferably includes a lip 19 sized and shaped for threaded or like engagement with a tube or other device, as shown in FIG. 2. With additional reference to FIG. 2, the distal end of the cannula body 14 may have a smaller diameter portion 22 for use in attaching the valve assembly 10 to a sheath 24 to form an introducer and for securing the end portion of the valve structure as will be explained. The sheath 24 can extend distally from the smaller diameter portion 22 of the valve housing 12 in a conventional fashion. For example, the proximal end 26 of the sheath 24 is shown to be flared over the smaller diameter portion 22. A strain relief sleeve 28 can be fitted over and/or attached to the proximal end 26 of the sheath 24 to maintain sufficient contact pressure between the proximal end 26 and the smaller diameter portion 22. An interventional device 29 can be extended through the sheath 24 and through the valve assembly 10 along a longitudinal axis LA, such that a seal is capable of being formed with the interventional device.

The term "interventional device" refers to any device, object, or structure, that supports, repairs, or replaces, is configured to support, repair, or replace, or that may be used, alone or in combination with other devices, objects, or structures, to support, repair, or replace a body part or a function of that body part. Examples of interventional devices include, but are not limited to, sheaths, catheters, wire guides, cardiac leads, vessel occlusion devices, filters, stents, stent grafts, and delivery and deployment devices.

An operable element 32 can also extend radially out from a cavity 35 of the cannula body 14 and is accessible to the end user on the exterior of the cannula body. The operable element 32 is attached to one of the ends of a valve structure disposed within the cavity 35 as will be explained. A slot 36 can be formed through the wall of the cannula body 14 for guiding the movement of the operable element 32, and thereby varying the diameter of the valve structure.

Figure 3:
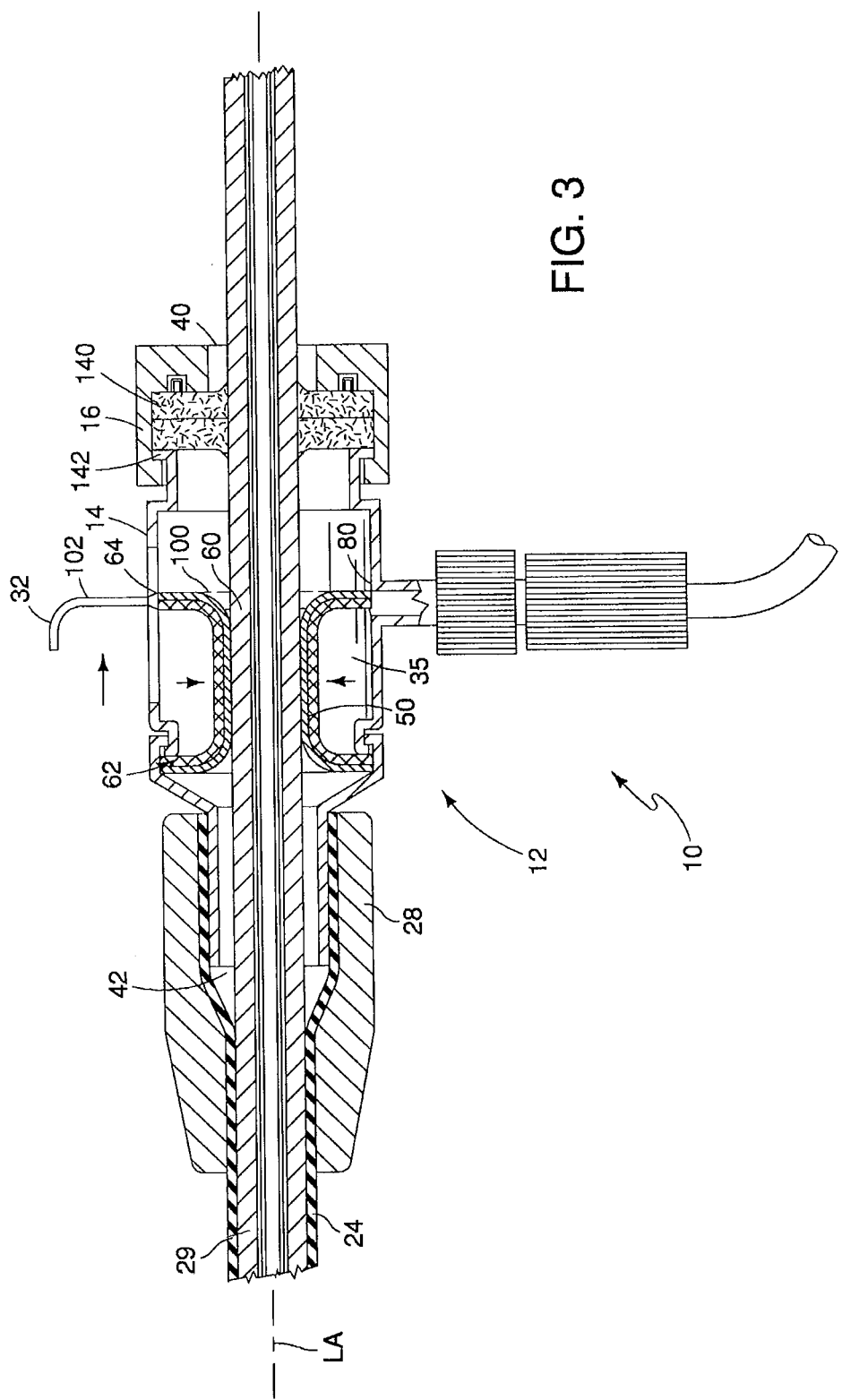
FIG. 3 is a longitudinal cross-sectional view of an introducer having a hemostatic valve device, with a valve structure in a closed position and an interventional device extending therethrough.

FIGS. 2-3 are longitudinal cross-sectional views of the valve assembly 10 with the sheath 24 and the interventional device 29 extending therethrough. The valve housing 12 includes a proximal, first end opening 40 and a distal, second end opening 42. An interior surface of the cannula body 14 and an interior surface of the end cap 16 can define the cavity 35 between the proximal and distal end openings 40, 42. The valve structure 50 can be disposed within the cavity 35 and coupled to the valve housing 12. The valve structure 50 can be movable between an open position (FIG. 2) and a closed, sealed position (FIG. 3) as described below. The valve structure 50 can have an inner radial surface 56 that defines a longitudinal channel 60 about the longitudinal axis LA within the housing cavity 35 between the proximal and distal end openings 40, 42. The channel 60 is sized and shaped for receiving one or more interventional devices of varying diameters. The diameter of the channel can vary between a first diameter and a second, lesser diameter, where the valve structure may completely close in on itself to form a seal when there is not an interventional device.

The valve structure 50 can be one of many shapes and sizes. In one example, as shown in FIG. 2, the valve structure 50 can be a tubular member having portions such as first and second end portions 62, 64. The first end portion 62 can be coupled to the valve housing 12. The second end portion 64 can be coupled to the operable element 32 and is movable relative to the first end portion 62. The change in the relative distance between the first and second end portions 62, 64 selectively varies the diameter of the channel 60 of the valve structure. Hence, by moving the operable element 32 that is connected to the second end portion 64 relative to the first end portion 62 to different positions within the slot 36, the channel diameter is adjustable to seal around interventional devices of different diameters. To this end, the valve structure can be formed to have any suitable channel diameter for receiving the desired size of the interventional device.

Figure 4A:
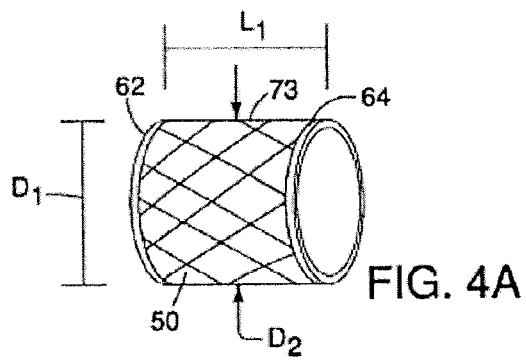
FIGS. 4A-4B are perspective views of a valve structure being moved between open and closed positions, respectively.
Figure 5:
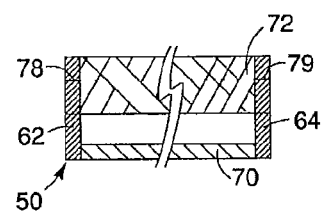
FIG. 5 is a partial cross-sectional view of a valve structure, depicting layers that form the valve structure.
Figure 4B:
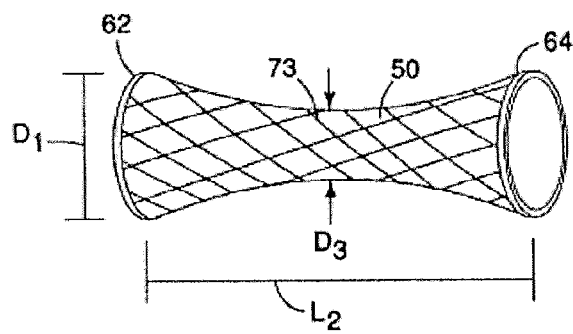

FIGS. 4A-4B depict the movement of the valve structure 50 between the fully open configuration and the fully closed configuration, respectively. The valve structure 50 can include one or more layers of biocompatible material. For example, FIG. 5 illustrates a cross-section of the wall of the valve structure 50, which includes a tubular sealing layer 70 and a tubular contractible layer 72 fitted over the sealing layer. It is preferred that the layers 70, 72 remain unattached to each of other, which is illustrated by the exaggerated spacing between the layers, to facilitate independent movement of the layers, although the ends of each layer may be in contact with one another. The arrangement with the unattached layers can provide for a greater range of axial and radial expansion and/or compression of the valve structure. The contractible layer 72 is configured to increase and/or decrease in diameter, while configured to decrease and/or increase in length respectively during relative movement between its ends. To this end, the contractible layer 72 is movable between an expanded configuration where the diameter is at its maximum and the length is at its minimum, and a contracted configuration where the diameter is at its minimum and the length is at its maximum.

In FIG. 4A, the valve structure 50 is in the fully open configuration. Here, the first and second end portions 62, 64 of the valve structure have an end diameter D1, such as, e.g., about 7 mm (0.3 inches). The valve structure has a first axial length L1, such as, e.g., about 10 mm, and at least a first sealing diameter D2, substantially equal to the first diameter D1, along an intermediate sealing region 73 of the valve structure 50 capable of sealing against the largest interventional device, such as, e.g., a 22-French interventional device. Here, the sealing layer 70 is at its relaxed natural configuration (i.e., pre-tensioned configuration), and the contractible layer is at its expanded configuration. In FIG. 4B, the valve structure 50 is in the fully closed configuration by application of an axial force at the second end portion 64 sufficient to move the second end portion axially away from the first end portion 62. Here, the end diameter D1 of the first and second end portions 62, 64 of the valve structure can remain constant during movement. The length of the valve structure can be increased to a second axial length L2, such as, e.g., about 30 mm, whereas the sealing diameter of the sealing region 73 can be decreased to a second sealing diameter D3, such as about 0.7 mm (0.03 inches) or smaller, that is suitable to seal against the smallest interventional device, such as, e.g., a wire guide, or to seal against itself. Here, the sealing layer has a tensioned configuration as a result of stretching and the elongation of the sealing layer. The contractible layer when moving to the contracted configuration can apply external pressure to the sealing layer to facilitate the reduction of the diameter of the sealing layer in a tensioned configuration against an interventional device.

To this end, each of the layers 70, 72 can increase in diameter while decreasing in length independent from one another, and vice versa, during movement of the operable element. The layers can form a valve structure that includes a generally cylindrical main body and first and second end portions 62, 64 in the shape of an annular flange extending radially outwardly from the main body. At least one of the end portions may have a rigidity sufficient to maintain its shape during movement of the operable element. The main body may have a rigidity less than the rigidity of the end portions so that the body has a flexibility to be displaced during the housing movement. The valve structure can be shaped like a spool but can have other configurations, such as an accordion-type shape or an hourglass shape, as well as having other cross-sectional geometric shapes such as rectangular, triangular, diamond, or elliptical, which are described in U.S. Pat. No. 7,172,580 to Hruska, which is incorporated herein by reference in its entirety.

Figures 6A, 6B:
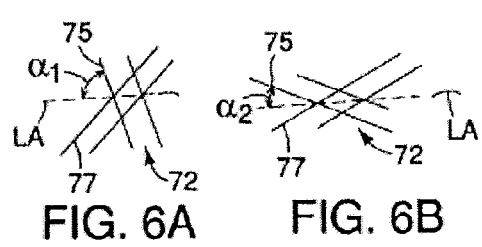
FIGS. 6A-6B illustrate movement of a braided layer of a valve structure.

The contractible layer 72 may apply a substantially uniform pressure along the sealing region 73 to urge the sealing layer 70 to contact with the interventional device to enhance the sealing capabilities of the sealing layer. As a result, there can be a reduced risk of infolding of the sealing layer or formation of gaps or channels along the sealing region 73. One such contractible layer is a braided structure made of braided or interwoven-material, extensible or inextensible fibers, strands, yarns, monofilaments, or multi-filaments. The filament materials for the braided structure can include polypropylene, polyester, polyethylene, polyamide (nylon), polyamide copolymers, silicone, polyurethane, or other biocompatible elastomers. The filament material can be strong enough to provide sufficient radial compressive strength when axially elongated when arranged in a braided structure. In one example, the filament material includes an elastomeric material, such as, e.g., a silicone rubber, having a durometer of about 35 to 50 on the Shore A hardness scale. Filaments are braided in a biaxial braid sometimes referred to as "Chinese finger trap" braid. With reference to FIGS. 6A-6B, the braided filaments extend in a helix configuration along the longitudinal axis LA, with a first set of filaments 75 having a common direction of winding but axially displaced relative to each other, and crossing a second set of filaments 77 axially displaced relative to each other but having an opposite direction of winding. The first and second sets of filaments 75, 77 can cross each other a first angle $\alpha 1$ with respect to the longitudinal axis LA when the net force along the length of the braided structure is zero. This is due to the constraint set by the filaments to move the contractible structure to the expanded configuration. The braided angle can decrease to a second angle $\alpha 2$ relative to the longitudinal axis at maximum radial compression (maximum lengthening) when an axial force is applied along the length of the braided structure. In one example, extensible filaments may be used in the braided structure to permit an increase in elongation of the valve structure. For instance, in the case where the filaments in the braided structure reach the second angle $\alpha 2$ before the maximum length of the valve is reached, the extensible filaments permit the end user to further elongate the braided structure to a smaller diameter for even a tighter seal around the interventional device.

Any number of filaments of any size, such as 0.15-0.6 mm diameter, can be interwoven into helical shape strands on a mandrel of a suitable diameter. The first set of filaments (one-half of the total number) are helically wound clockwise and the second set of filaments (one-half) are helically wound counterclockwise such that each clockwise filament is adjacent and interbraided with a counterclockwise filament. The filaments can be helically wound at the first angle $\alpha 1$ such that the relationship is represented by the following equation: $\cos(\alpha 1)=A/B$. A is defined as wN—where N is the number of carriers and w is the width of the filaments, whereas B is defined as $2\pi(1-\mathrm{SQRT}(1-F))D$—where D is the diameter of the braided tube and F is the fraction of projected area covered by filaments (1.0-0.5). This equation is described in *Handbook of Composite Reinforcements* by Stuart Lee (John Wiley and Sons (1992)), which is incorporated herein by reference in its entirety. The filaments of the braided structure can be coupled to one another at both ends 78, 79 of the tubular braided structure such as by adhesive or soldering, as shown in FIG. 5, while the remaining intermediate portion of the braided structure between the coupled ends remains free to move accordingly. The braided structure can be heat treated, such as an annealing process, to set the desired braided configuration at rest.

The material of the sealing layer 70 can have sufficient elasticity or compliance for axial elongation and radial reduction to enhance sealing along the interventional device. To this end, the sealing layer 70 is movable between the pre-tensioned configuration where the diameter is at its maximum and the length is at its minimum, and the tensioned configuration where the diameter is at its minimum and the length is at its maximum. It is contemplated that the sealing layer may be configured to move between a pre-radially compressed, axially expanded configuration and a radially expanded, axially compressed configuration. The sealing layer can be formed from elastomeric materials such as silicone, urethane, or rubber, although any suitable composition known in the art for such purposes may be substituted. Alternative materials include polytetrafluoroethylene (PTFE); polyamide (e.g., nylon 12) material, a polyamide block copolymer (e.g., PEBA) and blends thereof (e.g., nylon 12/PEBA and PEBA/PEBA blends); polyolefins, polyolefin copolymers and blends thereof; polyesters (e.g., poly(ethylene terephthalate), PET); polyurethane copolymers with MDI, HMDI or TDI hard segment and aliphatic polyester, polyether or polycarbonate soft segment (e.g., Pellethane, Estane or Bionate); and polyester copolymers with 4GT (PBT) hard segment and aliphatic polyester or polyether soft segments (e.g., Hytrel, Pelprene or Arnitel)).

The flexibility and the thinness of the sealing layer may be considerably greater than the flexibility and thinness of the contractible layer. If desired, the valve structure, or preferably the inner radial surface of the sealing layer, can be coated with a lubricious coating, such as parylene, to improve the lubricity of the surface and facilitate the passage of the interventional device therethrough. Since the sealing layer is discrete from the contractible layer, it is desirable to form the sealing layer as thin as possible taking into consideration the tensile properties of the material and/or puncturability of the material. A suitably thin sealing layer can be advantageous in the prevention of infolding and the formation of gaps and/or channels. In one example, the sealing layer is a silicone tube with a 0.02-inch wall thickness.

The cannula body 14 and the end cap 16 can be made of a machined or injection molded relatively rigid polymeric material, such as such as acetal, polypropylene, ABS, nylon, PVC, polyethylene or polycarbonate. As illustrated, each of the aforementioned constituents includes a hollowed-out center portion to enable passage of an interventional device therethrough.

According to FIG. 2, the first end portion 62 of the valve structure 50 may be attached within the valve housing 12 by any suitable attachment mechanisms such as an adhesive, welding, soldering, molded into the housing, or the like so that leakage of the fluid from within the valve structure can be prevented. For example, the first end portion 62 can be attached along the interior surface 80 of the valve housing 12. The sealing layer 70 can have ends 82, 84 that are flared out to define a spool shaped tube or optionally may have radial flanges formed at the ends 82, 84. To this end, the first end 82 of the sealing layer forming a part of the first end portion 62 of the valve structure, along with the first end 78 of the contractible layer 72, can be captured within an inner radial recess 86 formed in the interior surface 80. In one example, a ring, such as a snap ring, can be sized to fit snuggly with the respective first ends 82, 78 to form a sealably tight mechanical interference fit. In the example shown, the cannula body 14 can be formed from at least two components, a primary portion 90 and a distal portion 92 that are coupled to one another. The distal portion 92 can include the inner radial recess 86. The primary portion 90 may include a radial lip 94 that fits within the inner radial recess 86 to form the mechanical coupling. A groove 96 can be formed along the outer wall of the primary portion 90 and is sized to receive an inner radial flange 98 formed at the end of the distal portion 92. The components all coupled to one another as shown can form a fluid tight seal. Gaskets, adhesives, and/or other sealants can be used to form the coupling and seal. Once coupled to one another, the first end portion 62 of the valve structure 50 is fixed in a secured position relative to the valve housing 12.

In FIG. 2, the operable element 32 can include a coupling element 100 (shown in dashed lines) and a trigger element 102 coupled to one another. The coupling element 102 can be configured for attachment with the second end portion 64 of the valve structure 50, whereas the trigger element 102 is extendable through the slot 36 formed in the wall of the cannula body 14. To this end, the end user can apply a force to the trigger element 102 of the operable element 32 in order to move the second end portion 64 of the valve structure 50 relative to the fixed first end portion 62, thereby opening or closing the valve structure.

Figure 7:
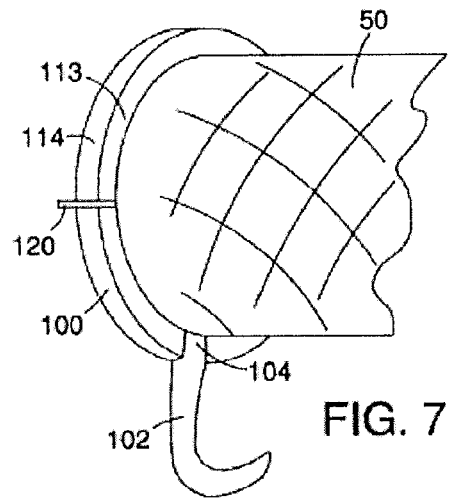
FIG. 7 is a perspective view of an operable element coupled to a valve structure.
Figure 8:
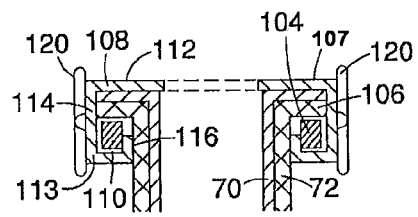
FIG. 8 is a partial cross-sectional view of the operable element of FIG. 7 coupled to the valve structure.

In FIGS. 7-8, the second end portion 64 of the valve structure 50 may be attached to the coupling element 100 by any suitable attachment mechanisms such as an adhesive, welding, soldering, molded into the housing, or the like so that leakage of the fluid from within the valve structure can be prevented. FIG. 8 depicts one example of the attachment mechanism. The coupling element generally forms a ring structure to permit passage of the interventional device therethrough and provide circumferential supports to the valve structure. The coupling element 100 can include a support ring 104, which can be attached to or integrally formed with the trigger element 102. A confronting surface 107 of the support ring 104 can be configured for engagement with the second end of the contractible layer 72 and/or the sealing layer 70. The coupling element 100 can also include a ring cap 106 that is configured to fit over the support ring 104 and the second ends of the contractible layer 72 and the sealing layer 70. For example, the ring cap 106 can include a wall 108 that defines a channel 110 sized and shaped to capture the support ring 104, the second end 79 of the contractible layer 72, and the second end 64 of the sealing layer 70 to form a sealably tight mechanical interference fit.

FIG. 8 depicts a cross-section of the wall 108 of the ring cap 106 in the form of a C-shape. The two opposite legs 112, 113 of the c-shaped wall 108 are spaced from one another to receive the components and form the mechanical coupling. The leg 114 of the wall 108 that interconnects the two opposite legs 112, 113 forms the radial outer surface of the ring cap 106. An inner lip 116 may be provided on the leg 113. The inner lip 116 can provide outer radial support to the layers 70, 72 and can inhibit the movement of the support ring 104 within the channel of the ring cap 106. The components when all coupled to one another as shown can form a fluid tight seal. Gaskets, adhesives, and/or other sealants can be used to form the coupling and seal. Once coupled to one another, the second end portion 62 of the valve structure 50 is fixed in a secured position relative to the coupling element 100 of the operable element 32.

The coupling element 100 is coupled within the cavity 35 of the valve housing in a manner to permit relative slidable longitudinal movement therebetween. To this end, the radial outer surface of the ring cap 106 is slidably engaged with the interior surface 80 of the valve housing 12. It is desirable to maintain the orientation of the operable element 32, and in particular the coupling element 100, to be perpendicular to the longitudinal axis LA of the valve housing 12 during movement. In one example, the leg 114 that defines the radial outer surface of the ring cap 106 can be widened to facilitate the stability and prevention of rocking or tilting of the operable element during movement.

One modification can include the provision of a guiding mechanism to stabilize the operable element and maintain its substantially perpendicular orientation with respect to the longitudinal axis during axial movement. For example, the ring cap 106 can include one more longitudinal guides 120 that are sized and shaped to fit within corresponding guiding channels (not shown) formed in the interior surface 80 of the valve housing. The guide 120 can include an elongate body that attaches to the surface of leg 114, and may extend past the edges of the ring cap to provide further stabilizing effects in the longitudinal direction. The operable element 32 is configured in a manner so that the pulling force applied thereto can be transferred to at least one point (preferable two or more points) between the coupling element 100 and the housing cavity 35 in order to maintain the operable element in a substantial perpendicular orientation relative to the longitudinal axis. For instance, when a single guide 120 is provided, it is desirable to place the single guide 120 in a location opposite the trigger element 102 to counteract moments created by the forces acting on the trigger element 102. When two guides are present, as shown in FIG. 8, the two guides can be located about 180 degrees apart, and preferably each about 90 degrees from the trigger element 102. As can be appreciated by those skilled in the art three or more guides can be provided along the ring cap. The guides 120 can stabilize and counteract moments created by movement of the operable element. One modification contemplated is to provide the guides in the form of ribs along the interior surface of the valve housing and the guiding channels in the form of grooves along the radial outer surface of the ring cap.

Relative axial movement between the operable element 32 and the valve housing 12 may be further enhanced in the form of selective incremental movement of the operable element to achieve a desired diameter. For example, a ratchet mechanism can allow for incremental changes in the diameter of the channel 60 of the valve structure 40. FIG. 9 depicts one example of the ratchet mechanism, with the operable element 32 having a pawl 130 that is engageable with a series of teeth or grooves 132 formed in the outer surface 134 of the cannula body 14. The teeth 132 can be disposed on either side of the slot 36 of the cannula body as shown or along both sides of the slot 132. The pawl 130 can extend longitudinally and substantially perpendicular to the operable element 32, i.e., extending in a direction generally parallel to the outer surface 134 of the cannula body. The tip 135 of the pawl 130 can extend substantially parallel to the operable element 32, i.e., extending in a direction generally perpendicular to the outer surface 134 of the cannula body to fit within the spacing between the teeth.

The tip 135 of the pawl 130 and the teeth 132 are configured to permit unrestricted movement in a first direction and to inhibit movement in a second direction, opposite the first direction. The teeth 132 can be uniform in shape having a first edge 136 with a first slope and a second edge 138 with a second slope that is steeper than the first slope. To this end, the tip 135 of the pawl 130 can slide along the profile of the teeth 132 along the first edge 136 of the teeth in the first direction to close the valve structure 50 to a smaller diameter. When the tip 135 enters the spacing between adjacent teeth, the second edge 138 is sized and shaped to inhibit the tip 135 from sliding in the second, opposite direction so that the seal can be maintained between the valve structure and the interventional device. To allow the valve structure to be opened to a larger diameter, the tip 135 can be released from its position by deflecting or lifting the tip 135 of the pawl 132 over the corresponding second edge 138. It can be appreciated by those skilled in the art that other ratcheting mechanisms are possible for modification to the system, such as, e.g., threaded attachment between the cannula body 14 and the end cap 16. It is contemplated that other ratcheting mechanisms may be substituted for achieving this action.

In FIG. 2, a sealing member 140 can be disposed within the valve housing 12, which is located proximal to the valve structure 50 in between the valve structure 50 and the end cap 16. The sealing member 140 can provide additional sealing with or without the presence of the interventional device 29. Further, the sealing member 140 can provide an additional support to the interventional device to inhibit radial movement of the interventional device when suspended within the valve housing.

In one example, the sealing member 140 includes one or more disks in an elongated passageway of a device through which fluids may be controllably passed into or out of the body. Such disks have opposing surfaces and often include one or more slits or apertures that extend at least partially across each of the surfaces and inwardly toward the interior of the disk. The thickness of the disk can vary so that the central region of the disk has a greater thickness to inhibit tearing of the slit or aperture during use. Preferably, valve disks have a slit or aperture on each face thereof, which each slit or aperture may be oriented in different patterns. The slit or aperture may extend either partially or fully through the disk. A generally axial opening is provided between the slits or apertures to provide a sealable path for insertion of the interventional device through the disks. Examples of such disks are described, e.g., in U.S. Pat. Nos. 5,006,113 and 6,416,499, which are incorporated herein by reference in their entirety. These disks are generally effective for sealing large diameter devices, but may be less effective for sealing smaller diameter devices. This may be especially true when a smaller diameter device is introduced through a disk following the earlier passage of a larger diameter device. Valve disks are preferably conventional check flow disks. Such valve disks are commercially available, and may be obtained, for example, from Cook Medical Inc. (Bloomington, Ind.), under the name CHECK-FLO® valves. Those skilled in the art will appreciate that any number of disks may be utilized.

The sealing member 140 may be assembled in the following manner. Initially, one or more valve disks are aligned in a desired orientation, and loaded at the end 142 of the cannula body 14. The end 142 can be configured as a radial flange. The valve disks can be made of a silicone material or other sealing materials known in the art. The end cap 16 can be placed over the end 142 of the cannula body 14, e.g., via a snap fit relationship, to capture the disks therebetween in a secured position. The valve disks may be compressed into the space between the cannula body 14 and the end cap 16, as shown in FIG. 2. A thin layer of a sealing lubricant, such as RTV silicone, can be placed between the end cap 16 and the cannula body 14 to provide a seal at their interface. In this case, the sealing lubricant acts in the nature of a gasket. The end cap 16 may have an annular groove 144 along its inner face 145. The annular groove 144 is configured to form a mating relationship with an annular protrusion 146 formed in the confronting surface 148 of the disk to inhibit dislodgment of the disk from the valve housing.

Operation of the valve assembly 10 to open and close the valve structure 50 will now be described. The valve structure 50 can be moved between the open and closed positions by relative axial movement between the operable element 32 and the cannula body 14 between a first position (FIG. 2) and a second position (FIG. 3) to move the second end portion of the valve structure relative to the first end portion. Although reference is made to first and second positions, the operable element may be movable through a number of positions intermediate the first and second positions, where the first position is a starting position and the second position is an ending position. In the first or starting position, the second end portion is positioned a first distance away from the first end portion to form a valve structure with a larger diameter. This first position can allow the valve structure 50 to be displaced radially outward away from the longitudinal axis LA so that the diameter of the channel can be increased to a larger diameter. The relative position of the operable element 32 and the cannula body 14 in the first or starting position may apply or increase an axial compression to the valve structure 50 for radial movement away from the longitudinal axis LA. Alternatively, to facilitate the movement of the valve structure to the open position, the valve structure may resiliently return to the open position when the valve structure is elastic and biased in an open position.

In the second (intermediate or ending) position, the second end portion is positioned a second, greater distance away from the first end portion to form a valve structure with a smaller diameter. Movement to this second position can permit the valve structure 50 to move radially inward toward the longitudinal axis LA so that the diameter of the channel is reduced to a smaller diameter. The relative position of the operable element and the cannula body 14 in the second position may apply a tension to the valve structure 50 to facilitate radial movement toward the longitudinal axis LA. Alternatively, to facilitate the movement of the valve structure to the closed position, the valve structure may resiliently return to a closed position when the valve is elastic and biased in the closed position.

The multi-layer valve structure having the discrete unattached layers (e.g., the bi-layer structure including the biaxial braided layer and the solid inner sealing layer) can increase the range of diameter for adjustability and reduce the force needed to adjust the diameter over valve structures with laminated or embedded structures. For example, the sealing layer can independently lie over the interventional device regardless of the position of the contractible layer. This allows for independent selection of the sealing layer thickness to be as small as possible to further inhibit infolding or gapping of the sealing layer along the interventional device. Moreover, the contractible layer is free to move without being restricted by the sealing layer due to lamination or bonding or by the material of the sealing layer residing within the spacings between the braided filaments when heat melted. When the contractible layer (e.g., the braided filaments) and the sealing layer are made for extensible materials, the valve structure is permitted to achieve smaller diameters when the layers are elongated due to stretching. The braided structure forming the contractible layer can provide substantially uniform mechanical external support and pressure along the sealing layer in order for the sealing layer to maintain sealing contact with the interventional device.

Drawings in the figures illustrating various embodiments are not necessarily to scale. Some drawings may have certain details magnified for emphasis, and any different numbers or proportions of parts should not be read as limiting, unless so-designated in the present disclosure. Although certain features of the valve device are only described with respect to certain embodiments and figures, it can be appreciated by those skilled in the art that the invention is not limited to any one of these features or embodiments but may reside in two or more combined features or embodiments together. Thus, those of skill in the art will appreciate that embodiments not expressly illustrated herein may be practiced within the scope of the present invention, including those features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

What is claimed is:

1. An introducer for use in inserting an interventional device into a body vessel of a patient, the introducer comprising:
   a housing having a first end opening, a second end opening, and an interior surface defining a housing cavity between the first and second end openings; and
   a valve structure coupled within the housing cavity, the valve structure having an inner radial surface defining a tubular channel along a longitudinal axis with a sealing region at least partially between the first and second end openings, the valve structure movable between a first configuration and a second configuration, wherein in the first configuration the sealing region has a first diameter and the valve structure has a first axial length, and in the second configuration the sealing region has a second diameter less than the first diameter and the valve structure has a second axial length greater than the first axial length,
   wherein the valve structure further comprises a contractible structure and a sealing structure, the sealing structure disposed inside of the contractible structure, wherein the sealing structure is unattached to the contractible structure at least along the sealing region of the valve structure to permit independent expansion and contraction therebetween in response to movement of the valve structure between the first and second configurations.

2. The introducer of claim 1, further comprising a sheath to extend distally from the second end opening of the housing, the sheath defining a conduit to receive an interventional device, the conduit in communication with the channel of the valve structure.

3. The introducer of claim 1, wherein the valve structure has a first end and a second end, one of the ends fixed within the housing cavity, the other of the ends movable relative to the fixed end along the longitudinal axis.

4. The introducer of claim 1, wherein the contractible structure comprises a braided filament.

5. The introducer of claim 1, further comprising an operable element having a coupling element coupled to the second end of the valve structure and a trigger element to extend from the coupling element to outside the housing.

6. The introducer of claim 5, wherein the coupling element further comprises a guiding mechanism to stabilize the operable element during movement of the valve structure between the first and second configurations.

7. The introducer of claim 1, wherein each of the contractible structure and the sealing structure comprises an extensible material to permit elongation of the structures during movement of the valve structure to the second configuration.

8. The introducer of claim 1, further comprising a ratchet mechanism to provide incremental movement of the valve structure between the first and second configurations.

9. The introducer of claim 1, further comprising a sealing element coupled within the housing cavity.

10. A hemostatic valve device comprising:
    a housing having a first end opening, a second end opening, and an interior surface defining a housing cavity between the first and second end openings;
    a valve structure having a first end and a second end, the first end of the valve structure securely fixed to the housing, the valve structure having an inner radial surface defining a longitudinal passageway for an interventional device, the valve structure having a sealing region at least partially between the first and second ends for sealable contact with the interventional device; and
    an operable element coupled to the second end of the valve structure, the operable element is movable between a first position and a second position, wherein, in the first position, the valve structure has a first configuration in which the sealing region has a first diameter and the valve structure has a first axial length, and in the second position, the valve structure has a second configuration in which the sealing region has a second diameter less than the first diameter and the valve structure has a second axial length greater than the first axial length.

11. The device of claim 10, wherein the operable element comprises a coupling element having a ring shape sized to fit within the housing cavity.

12. The device of claim 11, wherein the coupling element comprises a ring support and a ring cap, the ring cap having an interior sized to capture the ring support and the second end of the valve structure in a secured relationship.

13. The device of claim 11, wherein the operable element comprises a trigger element to extend out of the housing cavity from the coupling element.

14. The device of claim 13, further comprising a slot formed in a wall of the housing sized to receive the trigger element and permit movement of the trigger element therein.

15. The device of claim 14, further comprising a series of ratcheting grooves formed in the housing, and the operable element further comprises a pawl operable to interface with the grooves to provide incremental movement of the operable element between the first and second positions.

16. The device of claim 10, wherein the valve structure comprises a tubular biaxial braided sleeve and a tubular sealing sleeve, the sealing sleeve disposed inside of the braided sleeve and is discrete from the braided sleeve.

17. A method of introducing an interventional device to a target site in a body vessel of a patient, comprising:
    inserting an interventional device through a longitudinal passageway of a hemostatic valve device in a first configuration, the valve device comprising a housing having a first end opening, a second end opening, and an interior surface defining a housing cavity between the first and second end openings, and a valve structure coupled within the housing cavity, the valve structure having an inner radial surface defining the longitudinal passageway of the valve device, the valve structure comprising a contractible structure and a sealing structure, the sealing structure disposed inside of the contractible structure and unattached to the contractible structure to allow for independent movement therebetween, the valve structure in the first configuration forming a first diameter sized to receive the interventional device and a first axial length; and
    moving a first end of the valve structure relative to a second end of the valve structure to move the valve structure to a second configuration, the valve structure in the second configuration forming a smaller, second diameter sized to seal along the interventional device and a longer, second axial length.

18. The method of claim 17, wherein the contractible structure comprises a biaxial braided filament.

19. The method of claim 18, wherein the valve device comprise an operable element having a coupling element coupled to an end of the valve structure, and a trigger element to extend from the coupling element to outside the housing, wherein in response to force applied to the trigger element the valve structure moves between the first and second configurations.

20. The method of claim 18, wherein the valve device is coupled to a sheath having a lumen in communication with the longitudinal passageway of the valve structure, wherein the interventional device is inserted within the sheath.

* * * * *